United States Patent [19]

Preziosi

[11] Patent Number: 4,871,091

[45] Date of Patent: Oct. 3, 1989

[54] DISPOSABLE PACKAGE FOR LIQUIDS

[75] Inventor: Robert Preziosi, West Orange, N.J.

[73] Assignee: Mason-Keller Corporation, Roseland, N.J.

[21] Appl. No.: 250,611

[22] Filed: Sep. 29, 1988

[51] Int. Cl.⁴ .......................................... B65D 37/00
[52] U.S. Cl. ..................... 222/92; 222/107;
    222/541; 222/420; 206/530; 206/532; 206/438;
    206/484; 206/631; 206/633; 604/295
[58] Field of Search ................ 222/92, 107, 541, 420,
    222/490, 206, 212, 215; 604/295, 310; 206/530,
    532, 438, 484, 631, 633; 383/35, 59, 906, 107;
    D9/302

[56] References Cited

U.S. PATENT DOCUMENTS

| | | | |
|---|---|---|---|
| 2,552,870 | 5/1951 | Scherer | 222/107 |
| 2,648,463 | 8/1953 | Scherer | 222/107 |
| 2,861,572 | 11/1958 | Hind et al. | 604/295 |
| 3,184,121 | 5/1965 | Volckening | 222/541 X |
| 3,741,384 | 6/1973 | Cloud | 222/107 X |
| 3,862,684 | 1/1975 | Schmitt | 222/107 X |
| 3,917,116 | 11/1975 | Mason | 222/92 |
| 3,924,745 | 12/1975 | Hannemann et al. | 222/541 X |
| 3,995,739 | 12/1976 | Tasch et al. | 206/484 |
| 4,537,308 | 8/1985 | Hollander, Jr. | 206/484 |

FOREIGN PATENT DOCUMENTS 832056 4/1960 United Kingdom ............... 222/107

Primary Examiner—Joseph J. Rolla
Assistant Examiner—David H. Bollinger
Attorney, Agent, or Firm—Sherman and Shalloway

[57] ABSTRACT

A package for shipping, storing and controlled dispensing of a unit or single use quantity of liquid comprises a pair of flexible, liquid-impermeable sheets superposed one over the other. Each of the sheets comprises a first substantially rectangular section and a second substantially rectangular section, having different widths, and a transition section interconnecting the other two sections. One of the sheets has a recess formed therein which defines a pocket receivable of a unit or single use quantity of liquid. The other sheet defines a cover extending across and covering the recess. The recess also includes a portion defining an elongated and narrow spout extending outwardly of the pocket. The sheets are hermetically sealed to one another about their periphery completely about the recess. The "seal" may be manually peeled back in the region of the spout to open the package. The portions which peel back and the portions of the package proximate the opening are shaped so as to arcuately taper back from the opening, thereby eliminating any sharp edges in the vicinity of the opening. The package is particularly suitable for use with "eye drops".

7 Claims, 2 Drawing Sheets

U.S. Patent  Oct. 3, 1989  4,871,091
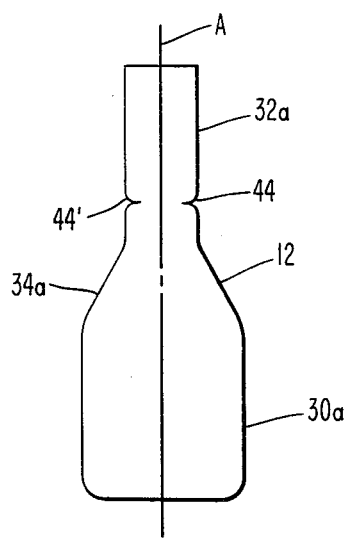
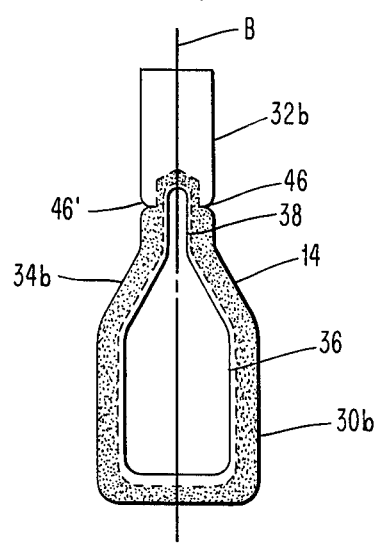
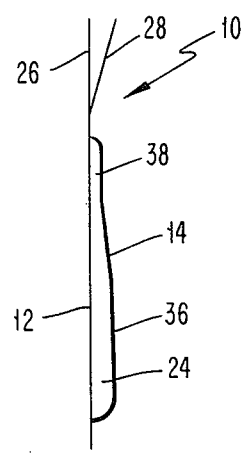
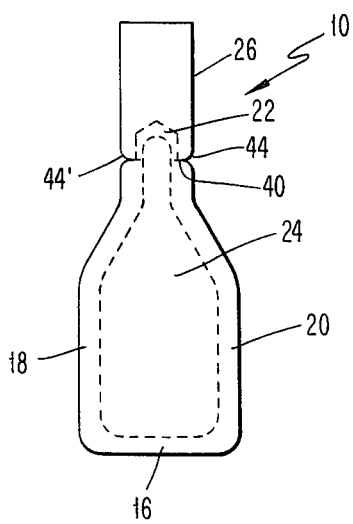
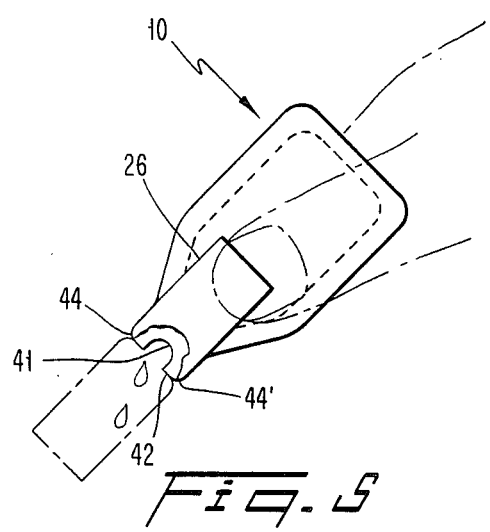

DISPOSABLE PACKAGE FOR LIQUIDS

BACKGROUND OF THE INVENTION

(1) Field of Invention

The present invention relates to a package for shipping, storing and controlled dispensing of a unit or single use quantity of a liquid. More particularly, the present invention relates to packages for eye drops, i.e. liquids for topical application to the eye.

(2) Description of Prior Act

Packages which are destined for a single use in the dispensing of a filling contained therein are known in various forms. For example, U.S. Pat. No. 3,924,745, to Hannemann et al, discloses a package comprising a single layer material having an interior cavity, surrounded on all sides by said material, forming a space to receive a filling. A hollow tubular body is connected to the cavity for passage of the filling material therethrough. A first longitudinal part of the hollow tubular body is surrounded fixedly by said material, and a second longitudinal part of the hollow tubular body is surrounded loosely by said material. The loosely surrounded portion and the fixedly surrounded portion are divided by a "tear off" area whereby the material which loosely surrounds the hollow tubular body may be removed to open the package.

U.S. Pat. No. 3,995,739, to Tasch et al, discloses a sealable, autoclavable package. More particularly, there is disclosed a heat-sealed, peelable package sterilized by autoclaving at elevated temperatures comprising a pair of substrates, wherein at least one of the substrates has a continuous, generally peripheral coating securing the substrates together. The coating comprises 18.75 parts by weight polyvinyl acetate and about 5.8 parts by weight nitrocellulose. The coating retains its normal peelable characteristics despite exposure to autoclaving temperature.

U.S. Pat. No. 4,537,308, to Hollander, Jr., discloses a package comprising a cylindrical plastic tube closed at each end by an ultrasonic band seal. The seal at one end has a sealed region which is narrower than any other portion of the seal, whereby squeezing of the package produces an immediate one-shot dispensing of liquid contained therein by causing rupture of the narrow region of the seal. Notched seals can provide a "tear open" package.

U.S. Pat. No. Des. 248,732, to Vollmar, discloses a collapsible tube-like container wherein apparently a portion of the container material is formed as a ring to facilitate hanging of the container on a display rack, and wherein this ring portion of the container may be torn or cut off to open the container.

U.S. Pat. No. 3,184,121, to Volckening, discloses a package with a self-sealing closure. Specifically, the package is formed of two identical sections which comprise layers of a suitable material sealed together in zones that form and bound between them a commodity containing compartment and an elongated discharge passage the extremity of which is normally tightly and permanently sealed. Preferably, the portions of the layers forming the walls of the compartment are self-sustaining but resilient so as to provide for momentary pressing of said walls toward each other to force some of the fluent commodity through the discharge passage, after the discharge passage is cut open, and for subsequent resilient movement of said walls away from each other and toward their original condition, to create a partial vacuum in the compartment causing self-sealing of the elongated discharge passage.

U.S. Pat. No. 3,862,684, to Schmitt, discloses a method of producing aseptic packages, particularly ampoules. The method comprises forming a plurality of oppositely directed substantially identical indentations on a foil on each side of a fold line. Thereafter, folding the foil material along the fold line to align the indentations so that they form half portions of individual containers. The foil sections are sealed together so that they close the container around a juncture line. Each container indentation includes a neck portion terminating in an outwardly widening funnel opening adjacent the edge of the foil material. The individual containers are then filled through the funnel and the neck portion is thereafter sealed directly below the bottom of the funnel. The area adjacent the seal and the juncture line is provided with tear lines to facilitate removal and opening of individual packages.

U.S. Pat. No. 3,917,116, to Mason, discloses a controlled flow liquid disposable unit package for single use packaging and dispensing of liquid commodities. In particular, a pad having liquid absorbed therein is sealed within the package to aid in containing liquid within the pocket, preventing inadvertent rupture of the pocket and aiding in control of liquid dispensing.

However, the aforementioned containers are variously difficult to fabricate and/or difficult in control of dispensing. Moreover, all of these containers provide sharp edges in close proximity to the containers opening, thus, presenting a danger in their use with eye drops. Additionally, it is difficult to prevent particulate matter, e.g., picked up from absorbent pads, from being dispensed with the liquid commodity. This latter problem is particularly exacerbated in the case of eye drops.

SUMMARY OF THE INVENTION

Accordingly, it is one object of the present invention to overcome the aforementioned difficulties with packages for the shipping, storing and controlled dispensing of a unit or single use quantity of liquid.

It is a further object of the invention to provide a package for shipping, storing and controlled dispensing of a unit or single use quantity of a liquid which is particularly efficacious for utilization with eye drops.

These and other objects of the invention, as will become apparent hereinafter, have been achieved by the provision of a package for shipping, storing and controlled dispensing of a unit or single use quantity liquid comprising: a unit or single use quantity of a liquid; a pair of flexible, liquid-impermeable sheets superposed one over the other, each of the sheets having a longitudinal axis and comprising a first substantially rectangular section of a first pre-determined width, a second substantially rectangular section of a second pre-determined width, the second pre-determined width being less than the first pre-determined width, and a transition section intermediate the first and second sections having a width tapering from the first pre-determined width adjacent the first section to the second pre-determined width adjacent the second section, one of the sheets having a recess, co-axial with the longitudinal axis, pre-formed therein defining a pocket substantially disposed within the first section and the transition section of the sheet, the pocket having a volume only slightly larger than the volume of the unit or single use quantity of liquid, the other of the pair of sheets defining a cover extending across and covering the recess enabling compression of the pocket and pressurization of the liquid by squeezing thereof between a user's thumb and forefinger without contaminating the liquid, the sheets being of sufficient resilience and flexibility to enable expansion of the pocket and cessation of pressurization of the liquid upon release of such user compression thereof, the recess comprising a portion defining an elongated and narrow spout portion, co-axial with the longitudinal axis, extending generally outwardly of the pocket from the transition section in the second section; sealing means for hermetically sealing the sheets together peripherally completely around the pocket and spout portion to protect the liquid from contamination and being manually peelable in the region of the spout to enable manual peeling back of the sheets in the region of the spout to a controlled extent less than the length of the spout portion to provide a restricted opening near the outboard end of the spout portion and an aseptic annular rim defined by a portion of the peeled sheets so that during expression of pressurized liquid through the opening the liquid only touches material theretofore previously sealed to retain the liquid sterile as it is expressed outwardly through the spout portion and the opening, the sealing means forming a stop line which defines a generally straight line edge substantially perpendicularly disposed to the longitudinal axis across the second section in the region of the spout, the stop line peripherally permanently affixing the sheets one to the other; means for defining an arcuately shouldered notch centered at each end of the stop line in each of the pair of sheets so that when the outboard ends of the second sections are peeled back to the stop line, and folded back upon respective transition sections, the portion of the sheets proximate the aseptic annular rim arcuately taper backwardly from the aseptic annular rim.

BRIEF DESCRIPTION OF THE DRAWING FIGURES

FIG. 1 is a plan view of a top sheet for the formation of a package in accordance with the present invention.

FIG. 2 is a plan view of a bottom sheet for the preparation of a package in accordance with the present invention.

FIG. 3 is a side view of a package in accordance with the present invention.

FIG. 4 is a schematic view of a package in accordance with the present invention.

FIG. 5 is a view of the package in accordance with the present invention, in use.

DETAILED DESCRIPTION OF THE INVENTION

Turning now to the drawing figures, there is shown and illustrated a unit package in accordance with the present invention designated generally by the reference character 10. The package 10 may be comprised of a top sheet 12 and a bottom sheet 14 sealed together along an end portion 16, along side portions 18 and 20 and head portion 22 extending between the side portions 18 and 20 at the ends thereof remote from end portion 16 thereby providing a sealed pocket 24 completely contained by the peripherally sealed end portion 16, side portion 18, side portion 20 and head portion 22 (the outline of which is shown in dotted lines in FIG. 4). The remaining portion of top sheet 12 and the remaining portion of bottom sheet 14 are preferably unsealed from each other to define a pair of flap portions 26 and 28 at the end of the package remote from end portion 16. Each of top sheet 12 and bottom 14 may be symmetrical about a longitudinal axis, A and B, respectively. Each of the sheets, 12 and 14, comprises a first substantially rectangular section, 30a and 30b, of a first pre-determined width, a second substantially rectangular section, 32a and 32b, of a second pre-determined width, which is less than the first pre-determined width, and a transition section, 34a and 34b, intermediate the first and second sections, having a width tapering from the first predetermined width adjacent the first section to the second predetermined width adjacent the second section.

The bottom sheet 14 has a recess 36, co-axial with the longitudinal axis B, performed therein defining the pocket 24 which is substantially disposed within the first rectangular section 30b and the transition section 34b of the bottom sheet 14. The pocket 24 may have a volume only slightly larger than the volume of the unit or single use quantity of liquid which is to be contained within the final package.

The top sheet 12 may be superposed over the bottom sheet 14 with the longitudinal axis A aligned with the longitudinal axis B, so as to form a cover extending across and covering the recess 36 enabling compression of the pocket 24 and pressurization of the liquid by squeezing thereof between a user's thumb and forefinger without contamination of the liquid contained within the pocket 24. The top sheet 12 and the bottom sheet 14 are of sufficient resilience and flexibility to enable expansion of the pocket and cessation of pressurization of the liquid upon release of such user compression thereof. The top sheet and the bottom sheet may be formed of any material having the requisite degree of resilience and flexibility so long as they are also impermeable to the liquid which is to be contained within the package. Suitable materials for the formation of such packages are known in themselves in the art, however, exemplary of such materials are thermoplastic resins and metallic foils, with aluminum foil being particularly preferred.

The recess further comprises a portion forming an elongated and narrow spout 38 which is co-axial with the longitudinal axis B, and extends generally outwardly of the pocket 24 from the transition section 34b into the second section 32b.

As shown by the stipling in FIG. 2, an adhesive coating may be applied to the surface of bottom sheet 14 so as to form a hermetic field between bottom sheet 14 and top sheet 12 which completely encompasses the recess 36. Preferably, the adhesive is a heat activatable adhesive, such as a thermoplastic, so that upon assembly and pressing between mating heated dies defining the end portion 16, the side portion 18, the side portion 20 and the head portion 22, the package will be formed as aforesaid. A stop line 40 which defines a generally straight line edge substantially perpendicular disposed to the longitudinal axis across the second section in the region of the spout 38 may be formed by welding along the straight line, so as to peripherally permanently affix the sheets 12 and 14 one to the other. The adhesive utilized, at least in the spout area, allows the sheets 12 and 14 to be manually peeled one from the other so as to provide a restricted opening 41 near the outboard end of the spout portion and aseptic annular rim 42 defined by a portion of the peeled sheets so that during expression of pressurized liquid (as shown in FIG. 5) through the opening the liquid only touches material theretofore previously sealed to retain the liquid sterile as it is expressed outwardly through the spout portion and the opening. By providing the stop line 40, a limit is placed on the degree of peeling apart of the sheets 12 and 14 by manual force exerted on flaps 26 and 28.

An arcuately shouldered notch 44, 44' is formed at each end of the stop line and centered on the stop line in sheet 12 and similarly an arcuately shouldered notch 46 and 46 prime is formed at each end of the stop line and centered on the stop line in sheet 14. By the provision of these arcuately shouldered notches, when the flaps 26 and 28 are peeled back to the stop line (as shown in FIG. 5) and folded back upon the package, the portions of the sheets 12 and 14 which are proximate aseptic annular rim 42 arcuately taper backwardly from the aseptic annular rim. Thus, no sharp (pointed) edge is formed at the peripheral edges of the package when in use. In a particularly preferred embodiment of the invention, the arcuately shouldered notches have shoulders formed in the shape of a quadrant of a circle, however, any smooth curve will provide a sufficiently dull edge so as to avoid possible injury to the user of the package.

As shown in FIG. 5, when the present package is grasped between the thumb and forefinger (shown in phantom lines) of a user, with the flaps 26 and 28 folded back (shown in solid lines) from their normal position (shown in phantom lines) the provision of arcuately shouldered notches produces a rounded corner adjacent to the aseptic annular rim of the opening for expression of the liquid material in drop like form from the package. These rounded edges are particularly desirable when the liquid contained in the package constitutes a topical preparation for the eye, e.g. eye drops, whereby pointed edges are removed from the vicinity of application. Of course, the presently contemplated package may also be utilized with other materials such as food flavorings, vitamin drops, cosmetics, condiments, and the like.

By appropriate selection of the adhesive to be utilized with the present packaging system, packages constructed in accordance with present invention provide complete hermetic sealing with zero transmission of moisture and/or contamination. Further, by appropriate selection of the adhesive material, packages in accordance with the present invention may be autoclaved so as to be thereby rendered sterile and as heretofore pointed out, when the flaps 26 and 28 are folded backwardly, as shown in FIG. 5, an aseptic opening is provided.

What is claimed is:

1. A package for shipping, storing and controlled dispensing of a unit or single use quantity of liquid comprising:

a pair of flexible, liquid-impermeable sheets superposed one over the other, each of said sheets having a longitudinal axis and comprising a first substantially rectangular section of a first predetermined width, a second substantially rectangular section of a second predetermined width, said second predetermined width being less than said first predetermined width, and a transition section intermediate said first and second sections having a width tapering from said first predetermined width adjacent said first section to said second predetermined width adjacent said second section, one of said sheets having a recess, co-axial with its longitudinal axis, pre-formed therein defining a pocket substantially disposed within said first section and said transition section of said sheet, said pocket having a volume only slightly larger than the volume of said unit or single use quantity of liquid, the other of said pair of sheets defining a cover extending across and covering said recess enabling compression of said pocket and pressurization of said liquid by squeezing thereof between a user's thumb and forefinger without contaminating said liquid, said sheets being of sufficient resilience and flexibility to enable expansion of said pocket and cessation of pressurization of said liquid upon release of such user compression thereof, said recess further comprising a portion defining an elongated and narrow spout portion co-axial with said sheet longitudinal axis, extending generally outwardly of said pocket from said transition section into said second section;

sealing means for hermetically sealing said sheets together peripherally completely around said pocket and spout portion to protect said liquid from contamination and being manually peelable in the region of said spout to enable manual peeling back of the second portions of said sheets in the region of said spout to a controlled extent less than the length of said spout portion to provide a restricted opening near an end of said spout portion and an aseptic annular rim defined by a portion of said peeled sheets so that during expression of pressurized liquid through said restricted opening said liquid only touches material theretofore previously sealed to retain said liquid sterile as it is expressed outwardly through said spout portion and said restricted opening, said sealing means having a stop line which defines a generally straight line edge substantially perpendicularly disposed to said longitudinal axes across said second sections in the region of said spout, said stop line peripherally permanently affixing said sheets one to the other;

means defining an arcuately shouldered notch centered at each end of said stop line in each of said pair of sheets so that when the ends of said second sections are peeled back to said stop line, and folded back upon respective transition sections, the portions of said sheets proximate said aseptic annular rim arcuately taper backwardly from said aseptic annular rim.

2. The package according to claim 1, wherein said flexible, liquid impermeable sheets comprise metal foil.

3. The package according to claim 2, wherein said metal foil is aluminum.

4. The package according to claim 2, wherein said stop line comprises a weld line.

5. The package according to claim 1, wherein said sealing means comprises an adhesive.

6. The package according to claim 5, wherein said adhesive is heat activatable.

7. The package according to claim 1, wherein said arcuate shoulder is a quadrant of a circle.

* * * * *